United States Patent [19]

Afonso

[11] 4,382,949
[45] May 10, 1983

[54] 2-(AMINO ACID-THIO)-1-CARBAPEN-2-EM-3-CARBOXYLIC ACIDS AND CONGENERS

[75] Inventor: Adriano Afonso, West Caldwell, N.J.

[73] Assignee: Schering Corporation, Kenilworth, N.J.

[21] Appl. No.: 174,290

[22] Filed: Jul. 31, 1980

[51] Int. Cl.³ .................. C07D 487/04; C07D 205/08; A61K 31/40
[52] U.S. Cl. .............................. 424/274; 260/239 A; 260/245.2 T
[58] Field of Search .................... 260/245.27; 424/274

[56] References Cited

U.S. PATENT DOCUMENTS 4,172,144 10/1979 Bouffard ............................ 424/274

OTHER PUBLICATIONS

"Introduction to Stereochemistry", Mislow (ed) pp. 94-97 (1965).
"Topics in Current Chemistry #48: Stereochemistry II, pp. 26-27 (1974).
Kropp, Paper #231, and Wildonger, paper #232 in 11th Int. Congress of Chemotherapy, ICAAC, 19th Intersci-ence Conference on Antimicrobial Agents & Chemotherapy, Boston 1-5, 1979.

Primary Examiner—Mark L. Berch
Attorney, Agent, or Firm—Gerald S. Rosen; Bruce M. Eisen

[57] ABSTRACT 2-(Amino acid-thio)-1-carbapen-2-em-3-carboxylic acids and congeners having useful antibacterial activity are disclosed. The compounds are prepared in a reaction sequence starting with a 4-allylazetidinone.

3 Claims, No Drawings

2-(AMINO ACID-THIO)-1-CARBAPEN-2-EM-3-CARBOXYLIC ACIDS AND CONGENERS

The present invention relates to 2-(amino acid thio)-1-carbapen-2-em-3-carboxylic acids and congeners. More particularly, this invention relates to compounds of the formula I

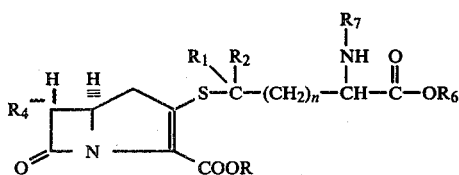

wherein
n is 0 to 4;
R is hydrogen, an alkali metal or quaternary ammonium cation or a metabolisable ester group;
$R_1$ and $R_2$ are independently hydrogen or lower alkyl;
$R_4$ is hydrogen, lower alkyl or a group of the formula

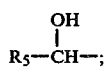

$R_5$ is hydrogen, lower alkyl, aryl, aralkyl, heteroaryl or heteroaralkyl;
$R_6$ is hydrogen, lower alkyl, allyl, aryl, aralkyl, an alkali metal or quaternary ammonium cation or a metabolisable ester group, or the group $OR_6$ is amino, lower alkylamino or an (N)-alpha-amino acid; and
$R_7$ is hydrogen, loweralkyl, aryl, aralkyl, arylsulfonyl, acyl, a 1,3-dicarbonyl adduct, a Schiff's base, an amidine or guanidine group.

The carbapenems of this invention are named by reference to the following formula

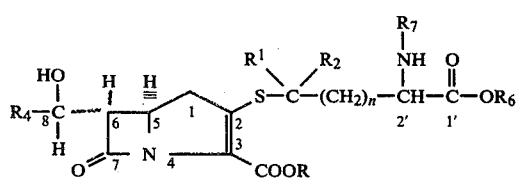

The lower alkyl groups referred to above contain 1 to 6 carbon atoms and are exemplified by methyl, ethyl, propyl, butyl, pentyl, hexyl, and the corresponding branched chain isomers thereof.

The term "acyl" as used herein denotes groups of the formula

wherein $R_8$ is lower alkyl, aralkyl, lower alkoxy, aryloxy, alkenyl or alkynyl of 2-6 carbon atoms, cycloalkyl of 4-6 carbon atoms, heteroaryl, heteroaralkyl, optionally substituted by hydroxy, thiol, alkylthio, lower alkyl, lower alkoxy, halogen, cyano, carboxy, nitro, amino, amino(lower)alkyl or halo(lower)alkyl such as trifluoromethyl. Representative of such groups are those such as benzyl, p-hydroxybenzyl, 4-amino-4-carboxybutyl, methyl, cyanomethyl, 2-pentenyl, n-amyl, p-heptyl, ethyl, 3- or 4-nitrobenzyl, phenethyl, 1,2-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl,3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl), 5-methyl-4-isozazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl 2-ethoxy-1-naphyl, 3-carboxy-2-quinoxalinyl, 3-(2,6-dichlorophenyl)-5-(2-furyl)-4-isoxazolyl, 3-phenyl-4-isoxazolyl, p-carboxymethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4-methoxy-5-isoxazolylmethyl, 2-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl) vinyl, phenyl, o-methoxyphenyl, o-chlorophenyl, o-phenylphenyl, p-aminomethylbenzyl, 1-(5-cyanotrizolyl) methyl, difluoromethyl, dichloromethyl, dibromomethyl, 1-(3-methylimidazolyl)methyl, 2- or 3-(4-carboxymethylthienyl)methyl, 2- or 3-(5-methylthienyl)-methyl, 2- or 3-(methoxythienyl)methyl, 2- or 3-(4-chlorothienyl)methyl, 2- or 3-(5-carboxythienyl)-methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, tetrazolylmethyl, cyclohexylamidinomethyl and other similar acyl groups found in conventional penicillin derivatives. The term also denotes an acyl residue derived from an alpha-amino acid of the L or D configuration. Typical alpha-amino acids utilizable are those such as alanine, glycine, isoleucine, leucine, phenylalanine and valine.

The term "aryl" as used herein refers to phenyl substituted by zero to three lower alkyl, lower alkoxy or halogen groups, e.g., p-tolyl, o-tolyl, m-tolyl, p-chlorophenyl, o-methoxyphenyl, 2-methyl-3-fluorophenyl, etc.

The term halogen as used herein refers to fluorine, chlorine, bromine and iodine.

Heteroaralkyl as used herein refers to lower alkyl groups substituted by a heteroaryl group.

As used herein, the term heteroaryl encompasses five- and six-membered heterocyclic groups containing from one to four nitrogen, oxygen or sulfur groups, optionally substituted by lower alkyl groups. Representative heteroaryl groups are those such as pyridyl, furanyl, thienyl, quinolinyl. The term is intended to cover all isomers, e.g., 2-pyridyl, 3-pyridyl and 4-pyridyl.

The lower alkoxy groups referred to above contain 1 to 6 carbon atoms and are exemplified by methoxy, ethoxy, propoxy, butoxy, pentoxy, hexoxy and the corresponding branched chain isomers thereof.

The term aralkyl denotes a lower alkyl group substituted by one or two aryl groups, e.g., benzyl, phenethyl, benzhydryl and the like, which each may be optionally substituted by one to three lower alkyl, lower alkoxy or halogen groups.

The term metabolisable ester group denotes an ester group which is metabolically or physiologically removed in the body. Typical metabolisable ester groups are those such as acetoxymethoxy, glycyloxymethoxy, L-valyloxymethoxy and acetylthiomethoxy. Two particularly useful metabolisable ester groups are the phthalidyloxy group and the pivaloyloxymethoxy group.

The term 1,3-dicarbonyl adduct as used herein refers to the addition product between the amino group of the amino acid carbon and a 1,3-dicarbonyl compound of the formula

wherein the R' groups can be alike or different and are selected from the group consisting of lower alkyl,-COO-lower alkyl or together may be part of a cyclic ring structure. Representative 1,3-dicarbonyl compounds utilized are those such as methyl acetoacetate, dihydroresorcinol, dimedone and acetyl acetone.

The terms amidine and guanidine as used herein refer to the derivatized amino group of the amino acid carbon wherein the derivatized amino group has the formula

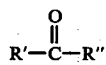

wherein X and Y are as defined in Belgian Pat. No. 848,545, (1977) the teachings of which are herein incorporated by reference.

The term Schiff's base as used herein refers to the addition of product between the amino group of the amino acid carbon and an aldehyde or ketone of the formula $$R'-\overset{O}{\underset{\|}{C}}-R''$$

where R' is an aryl group and R'' is hydrogen, lower alkyl or aralkyl.

The alkali metal salts may be derived from potassium, sodium, lithium, etc., with potassium and sodium being particularly preferred. The quarternary ammonium salts may be those such as pyridinium, procaine, N-methylglucamine, ethanolamine or diethanolamine.

The foregoing compounds possess several centers of chirality and are produced by the various processes as various isomeric mixtures. The present invention is directed to compounds of the preferred stereochemical configuration of formula I and to mixtures of it together with its enantiomers.

With respect to those in the penem nucleus itself, the preferred configuration of the carbon atoms at the 5 and 6 positions have the absolute stereochemistry R and S, respectively. The two hydrogen atoms attached to the 5 and 6 carbon atoms are thus trans to one another. The stereochemistry of the C-8 carbon atom may be designated as either R or S depending on the exact nature of the $R_5$ substituent. For instance, the compounds wherein $R_5$ is methyl will have the 8R stereochemistry. The most preferred stereochemical configuration for a compound of this invention wherein $R_5$ is methyl is designated 5R,6S,8R, and has the following representative spatial configuration

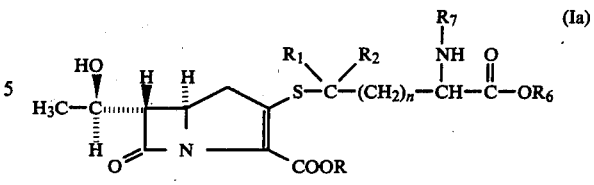

The preferred stereochemical configuration of all the compounds of formula I is that shown in formula Ia; however, the nomenclature may differ depending on the nature of the $R_5$ substituent. Wherein the $R_5$ group of formula I has a higher priority in the Cahn-Ingold-Prelog system, e.g., a 2-pyridyl group, a compound having the most preferred stereochemical configuration will be designated 5R, 6S, 8S, but be of the same relative spatial configuration at C-5, C-6 and C-8 as the 5R, 6S, 8R compound of formula Ia. These compounds additionally possess an asymetric center at the carbon atoms to which the $NHR_7$ and $COOR_6$ substituents are attached ("amino acid carbon") depending on the configuration of the starting materials. Most preferably this carbon atom will possess absolute stereochemistry of the R configuration. When naturally occurring amino acids are utilized as starting materials, the configuration at the amino acid carbon will thus be of the "R" or "D" and the "S" or "L" configurations.

Certain of the processes of this invention produce these compounds as their racemic mixtures, e.g., a 5R, 6S, 8R compound is produced with its enantiomer (mirror image), i.e., a 5S, 6R, 8S compound in the equal amounts when the starting compound is a racemic mixture. The two enantiomers may be separated by conventional means, e.g., by resolution by fractional crystallizations of optically active salt forms, e.g., the salts derived from optically active amino acids, (−)-brucine, or (+)- and (−)ephedrine. Alternatively, the compounds may be produced in their pure enantiomeric forms by utilizing optically active intermediates in the synthetic procedure.

Preferred compounds of formula I are those wherein $R_5$ is a lower alkyl group. Particularly preferred are those compounds of formula I wherein $R_5$ is a methyl group.

A most particularly preferred group of compounds of formula I encompassed by this invention are those wherein $R_5$ is methyl and the stereochemical configuration is designated 5R, 6S, 8R. Of these, the compounds wherein the amino acid carbon possesses the R configuration are most highly preferred. A particularly preferred compound is (5R,6S,8R,2'R)-2-[(2'-amino-2'-carboxyethyl)thio]-6-(1-hydroxyethyl)-1-carbapen-2-em-3-carboxylic acid, sodium salt.

The compounds of this invention possess antibacterial activity of both the gram-positive and gram-negative type. Thus, when tested in standardized microbiological assays, the compounds of this invention are active against such gram-positive organisms as *Staphylococcus epidermidis*, and *Bacillus subtilis*, and such gram-negative organisms as E. coli, Pseudomonas and Salmonella at test levels of 0.1 to 100 µg/ml. Additionally, they show activity against such organisms in the presence of penicillanase indicating a resistance to this enzyme and are inhibitors of beta-lactamases.

Thus, the present invention includes within its scope pharmaceutical compositions comprising an antibacterially effective amount of a carbapenem of formula I together with a compatible, pharmaceutically acceptable carrier or coating. Also included within this invention is the method of eliciting an antibacterial response in a warm-blooded animal having a susceptible bacterial infection which comprises administering to said animal a non-toxic, antibacterially effective amount of compound of formula I.

The dosage administered of the penems of this invention is dependent upon the age and weight of the animal species being treated, the mode of administration, and the type and severity of bacterial infection being prevented or reduced. Typically, the dosage administered per day will be in the range of 100–5000 mg, with 500–1000 mg being preferred.

For oral administration, the compounds of this invention may be formulated in the form of tablets, capsules, elixirs or the like. Likewise, they may be admixed with animal feed. They may also be applied topically in the form of ointments, both hydrophilic and hydrophobic, in the form of lotions which may be aqueous, non-aqueous or of the emulsion type, or in the form of creams.

The compounds of formula I may be utilized in liquid form such as solutions, suspensions and the like for otic and optic use and may also be administered parenterally via intramuscular injection.

The compounds of this invention are preparable by a reaction sequence starting with a compound of the formula II

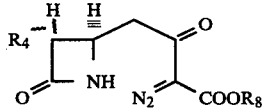

(II)

wherein $R_4$ is as hereinbefore defined and $R_8$ is a carboxy protecting group. Suitable carboxy protecting groups are those well-known in the art and include allyl, p-nitrobenzyl and the like. This compound of formula II is treated with rhodium acetate at a temperature of 40°–100° C. in a suitable organic solvent such as benzene or toluene to afford the intermediate of the formula III

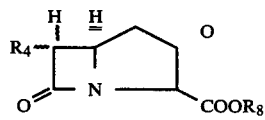

(III)

wherein $R_4$ and $R_8$ are as hereinbefore defined and the intermediate of formula III is then reacted with a dialkyl- or diarylchlorophosphate with the presence of an organic base to afford the intermediate of formula IV

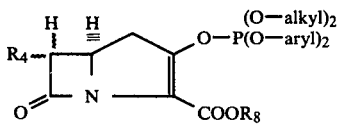

(IV)

wherein $R_4$ and $R_8$ are as hereinbefore defined. Suitable organic bases are those such as pyridine, triethylamine and diisopropylethylamine with the latter being particularly preferred. Suitable dialkyl- and diarylchlorophosphates are those such as di-n-butyl- and diphenylchlorophosphate.

The intermediate of formula IV is preferably not isolated but directly reacted with an amino acid of the formula V

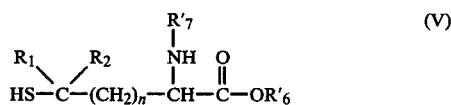

(V)

wherein $R_1$, $R_2$ and n are as hereinbefore defined, $R_6'$ is lower alkyl, aryl or aralkyl or another suitable carboxy protecting group, and $R_7'$ is lower alkyl, aryl, arylsulfonyl aralkyl, or a suitable amino protecting group, to afford the compound of formula VI

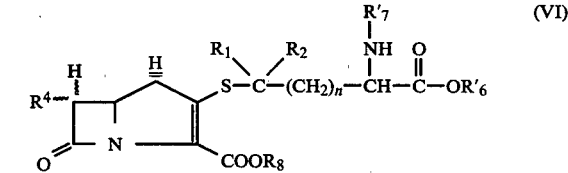

(VI)

wherein $R_1$, $R_2$, $R_4$, $R_6'$ $R_7'$ and $R_8$ are as hereinbefore defined. This reaction is preferably conducted in the presence of an acid acceptor, most preferably a weak organic base such as diisopropylethylamine or pyridine.

Removal of the protecting groups from the compounds of formula VI results in the products of formula I wherein $R_7$ is hydrogen, acyl, lower alkyl, aryl or aralkyl. The conventional amino protecting groups, e.g., benzyloxycarbonyl, p-nitrobenzyloxycarbonyl and benzhydryloxycarbonyl, and carboxy protecting groups, e.g., benzyl, p-nitrobenzyl and benzhydryl, can be removed by hydrogenation. Certain hydroxy protecting groups such as trichloroethoxycarbonyl may be removed by deprotection via zinc/acetic acid in a suitable aprotic solvent such as tetrahydrofuran. Most preferably, however, the allyl and allyloxycarbonyl protecting groups will be utilized for carboxy and amino groups. This group is most preferably removed by the procedure of Tsuji described in *Tetrahedron Letters*, 7, 613 (1979). The Tsuji deprotection procedure utilizes an amine salt of formic acid and a mixture of a palladium compound and triphenyl phosphine as the catalyst. This deprotection method is particularly suitable for the sensitive beta-lactam carboxylates of this invention.

The amino group of the compounds of formula I wherein $R_7$ is hydrogen may optionally be converted to their corresponding compounds wherein $R_7$ is a Schiff's base, for instance, as in U.S. Pat. No. 4,172,144, or to the compounds wherein $R_7$ is an amidine or guanidine, e.g., where the amino group is converted to the

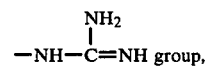

as described in ICAAC, 11th International Congress of Chemotherapy, 19th Interscience Conference on Antimicrobial Agents and Chemotherapy, Boston, Oct. 1–5, 1979, Papers 231 and 232.

Compounds preparable by the above reaction schemes include the following representative compounds of this invention each together with its enantiomer when prepared from racemic starting materials, and alone when prepared from chiral intermediates. The most highly preferred stereochemical isomers, i.e., the 5R, 6S, 8R, 2'R isomers are named, however, the corresponding isomers may be prepared by choice of suitable starting compounds:

(5R,2'R)-sodium 2-[(2-amino-2'-carboxyethyl)thio]-1-carbapen-2-em-3-carboxylate;

(5R,2'R)-sodium 2-[2'-amino-2'-carboxypropyl)thio]-1-carbapen-2-em-3-carboxylate;

(5R,2'R)-sodium 2-[(2'-amino-2'-carboxy-3',3'-dimethylethyl)thio]-1-carbapen-2-em-3-carboxylate;

(5R,2'R)-sodium 2-[(2'-acetylamino-2'-carboxyethyl)thio]-1-carbapen-2-em-3-carboxylate;

(5R,2'R)-sodium 2-[(2'-amino-2'-methoxycarbonylethyl)thio]-1-carbapen-2-em-3-carboxylate;

(5R,2'R)-sodium 2-[(2'-amino-2'-phenoxycarbonylethyl)thio]-1-carbapen-2-em-3-carboxylate;

(5R,2'R)-sodium 2-[2'-amino-2'-benzyloxycarbonylethyl)thio]-1-carbapen-2-em-3-carboxylate;

(5R,2'R)-sodium 2-[(2'-amino-2'-carboxybutyl)thio]-1-carbapen-2-em-3-carboxylate;

(5R,6S,8R,2'R)-sodium 2-[2'-amino-2'-carboxamidoethyl)thio]-6-(1-hydroxyethyl)-1-carbapen-2-em-3-carboxylate;

(5R,6S,8R,2'R)-2-[(2'-amino-2'-carboxyethyl)thio]-6-(1-hydroxyethyl)-1-carbapen-2-em-3-carboxylic acid, sodium salt;

(5R,6S,8R,2'R)-2-[(2'-amino-2'-carboxypropyl)thio]-6-(1-hydroxyethyl)-1-carbapen-2-em-3-carboxylic acid, sodium salt;

(5R,6S,8R,2'R)-2-[(2'-acetylamino-2'-carboxyethyl)thio]-6-(1-hydroxyethyl)-1-carbapen-2-em-3-carboxylic acid, sodium salt;

(5R,6S,8R,2'R)-2-[(2'-amino-2'-methoxycarbonylethyl)thio]-6-(1-hydroxyethyl)-1-carbapen-2-em-3-carboxylic acid, sodium salt;

(5R,6S,8R,2'R)-2-[(2'-amino-2'-phenoxycarbonylethyl)thio]-6-(1-hydroxyethyl)-1-carbapen-2-em-3-carboxylic acid, sodium salt;

(5R,6S,8R,2'R)-2-[(2'-amino-2'-benzyloxycarbonylethyl)thio]-6-(1-hydroxyethyl)-1-carbapen-2-em-3-carboxylic acid, sodium salt;

(5R,6S,8R,2'R)-2-[(2'-amino-2'-carboxy-3',3'-dimethylethyl)thio]-6-(1-hydroxyethyl)-1-carbapen-2-em-3-carboxylic acid, sodium salt;

(5R,6S,8R,2'R)-sodium-[(2'-amino-2'-carboxethylamidoethyl)thio]-6-(1-hydroxyethyl)-1-carapen-2-em-3-carboxylate;

(5R,6S,8R,2'R)-sodium-2-[(2'-amino'2''-carboxamidoethyl)thio]-6-(1-hydroxyethyl)-1-carbapen-2-em-3-carboxylate;

(5R,6S,8R,2'R)-sodium-2-[(2'amino-2'-carboxyethylamidoethyl)thio]-6-(1-hydroxyethyl)-1-carbapen-2-em-3-carboxylate;

(5R,6S,8R,2'R)-2-[(2'-amino-2'-carboxy-4'-methylpropyl)thio]-6-(1-hydroxyethyl)-1-carbapen-2-em-3-carboxylic acid, sodium salt;

(5R,6S,8R,2'R)-2-[(2'-amino-2'-carboxybutyl)thio]-6-(1-hydroxyethyl)-1-carbapen-2-em-3-carboxylic acid, sodium salt;

(5R,6S,8R,2'R)-2-[(2'methylamino-2'-carboxyethyl)thio]-6-(1-hydroxyethyl)-1-carbapen-2-em-3-carboxylic acid, sodium salt;

(5R,6S,8R,2'R)-2-[(2'-phenylamino-2'-carboxyethyl)thio]-6-(1-hydroxyethyl)-1 carbapen-2-em-3-carboxylic acid, sodium salt;

(5R,6S,8R,2'R)-2-[(2'-benzylamino-2'-carboxyethyl)thio]-6-(1-hydroxyethyl)-1-carbapen-2-em-3-carboxylic acid, sodium salt;

(5R,6S,8R,2'R)-2-[N-2,2,2-trifluoroacetyl-2'amino-2'-carboxyethyl)thio]-6-(1-hydroxyethyl)-1-carbapen-2-em-3-carboxylic acid, sodium salt;

(5R,6S,8R,2'R)-2-[(N-guanidino-2'-amino-2'-carboxyethyl)thio]-6-hydroxyethyl)-1-carbapen-2-em-3-carboxylic acid, sodium salt;

(5R,6S,8R,2'R)-2-[(N-trichloroethoxycarbonyl-2'-amino-2'-carboxyethyl)thio]-6-(1-hydroxyethyl)-1-carbapen-2-em-3-carboxylic acid, sodium salt;

(5R,6S,8R,2'R)-2-[(N-t-butoxycarbonyl-2'amino-2'-carboxyethyl)thio]-6-(1-hydroxyethyl)-1-carbapen-2-em-3-carboxylic acid, sodium salt;

(5R,6S,8R,2'R)-2-[(N-p-nitrobenzoxycarbonyl-2'-amino-2'-carboxyethyl)thiol]-6-(1-hydroxyethyl)-1-carbapen-2-em-3-carboxylic acid, sodium salt;

(5R,6S,8R,2'R)-2-[(N-benzyloxycarbonyl-2'-amino-2'-carboxyethyl)thiol]-6-(1-hydroxyethyl)-1-carbapen-2-em-3-carboxylic acid, sodium salt:

(5R,6S,8R,2'R)-2-[N-3''-methyl-2''-butenoatemethylester-2'-amino-2'-carboxyethyl)thiol]-6-(1-hydroxyethyl)-1-carbapen-2-em-3-carboxylic acid, sodium salt;

(5R,6S,8R,2'R)-2-[(N-1-(3-oxocyclohex-1-enyl)-2'-amino-2'-carboxyethyl)thiol]-6-(1-hydroxyethyl)-1-carbapen-2-em-3-carboxylic acid, sodium salt;

(5R,6S,8R,2'R)-2-[(N-2-(4-oxopent-2-enyl)-2'-amino-2'-carboxyethyl)thio]-6-(1-hydroxyethyl)-1-carbapen-2-em-3-carboxylic acid, sodium salt;

(5R,6S,8R,2'R)-sodium-2-[(2'amino-2'-carboxyethyl)thio]-6-ethyl-1-carbapen-2-em-3-carboxylate;

(5R,6S,2'R)-sodium-2-[(2'-amino-2'-carboxyethyl)thio]-6-(1-hydroxypropyl)-1-carbapen-2-em-3-carboxylate;

(5R,6S,2'R)-sodium-2-[(2'-amino-2'-carboxyethyl)thio]-6-[1-hydroxy-1-(4-pyridyl)methyl]-1-carbapen-2-em-3-carboxylate;

(5R,6S,2'R)-sodium-2-[(2'-amino-2'-carboxyethyl)thio]-6-(alpha-hydroxybenzyl)-1-carbapen-2-m-3-carboxylate;

(5R,6S,2'R)-sodium-2-[(2'-amino-2'-carboxyethyl)thio]-6-[1-hydroxy-2-(2-thienyl)ethyl]-1-carbapen-2-em-3-carboxylate;

(5R,6S,2'R)-2-[(2'-acetylamino-2'-carboxypropyl)thio]-6-(1-hydroxyethyl)-1-carbapen-2-em-3-carboxylic acid, sodium salt:

(5R,6S,2'R)-2-[(2'-amino-2'-methoxycarbonylpropyl)thio]-6-(1-hydroxyethyl)-1-carbapen-2-em-3-carboxylic acid, sodium salt;

(5R,6S,8R,2'R)-2-[(2'-N-D-alanyl-2'-amino-2'-carboxyethyl)thio]-6-(1-hydroxyethyl)-1-carbapen-2-em-3-carboxylic acid, sodium salt; and (5R,6S,8R,2'R)-2-[(2'-amino-2'-acyl-D-alanineethyl)thio]-6-(1-hydroxyethyl)-1-carbapen-2-em-3carboxylic acid.

This same series can also be prepared in the (5R,6S,8S,2'R), (5R,6S,8S,2'S) or (5R,6S,8R,2'S) configuration.

The starting materials of formula II are preparable from the known compound, 4-allylazetidin-2-one, via the following reaction sequence

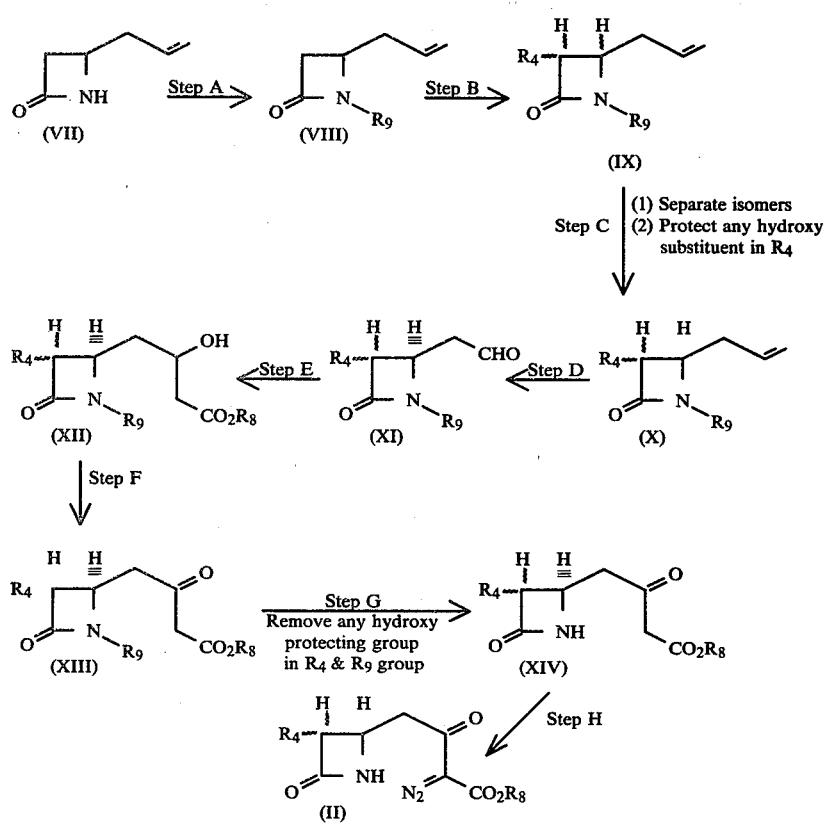

In Step A of Scheme I the 4-allylazetidin-2-one of formula VII reacted with a trialkylsilylchloride of the formula $R_9$-Cl wherein $R_9$ is the trialkylsilyl group, in the presence of an acid acceptor such as triethylamine so as to provide the N-protected compound of formula VIII. Preferably, the reaction is conducted in an organic solvent, particularly a halogenated hydrocarbon solvent such as chloroform or methylene chloride.

In Step B of Scheme I the compound of formula VIII is converted to the $R_4$-substituted compound of formula IX. Where the desired $R_4$ substituent is a hydroxyalkyl substituent the substituent is most conveniently added via treatment with lithium diisopropylamine and the appropriate aldehyde in an anhydrous aprotic solvent. A particularly suitable solvent is tetrahydrofuran.

The preparation of compounds of the formula IX from a compound of formula VII is also described in European Published Patent Application No. 8497 (1980).

In Step C, the various isomers of the compounds of formula IX are separated, if desired, by conventional means, i.e., chromatography or optically active salt formation. Additionally, if the $R_4$ substituent contains a hydroxy group, it is protected prior to Step D by a conventional hydroxy protecting group. Particularly suitable groups are those such as trichloroethoxycarbonyl and t-butyldimethylsilyl but others such as p-nitrobenzyloxycarbonyl or allyloxycarbonyl may also be utilized.

Step D converts the 4-allyl substituent of a compound of formula X to a 4-ethanal substituent in the compound of formula XI. Typically, this is accomplished by a conventional ozonolysis procedure.

In Step E, the aldehyde of formula XI is treated with a suitable acetate ester anion in an aprotic solvent such as tetrahydrofuran or ethyl ether. The product which results is the beta-hydroxyester of formula XII. A preferred acetate ester anion for use in this reaction is the lithium salt of allyl acetate produced by adding lithium di-isopropylamide to allyl acetate at low temperatures.

Conversion of compound XII to compound XIII in Step F is accomplished by treatment of the compound XII with an oxidizing agent such as chromium trioxide. Preferably, a halogenated hydrocarbon such as chloroform or methylene chloride is utilized as the solvent.

In Step G, any hydroxy protecting groups added in Steps A and/or C are removed. The method of removal depends upon the particular hydroxy- and N-protecting group utilized. For instance, trichloroethoxycarbonyl groups are removable with zinc/acetic acid while N-t-butyldimethylsilyl groups are removable with hydrocloric acid or amberlite 401-S(F-) resin.

Step H involves diazonation of the compound of formula XIV to provide the desired compound of formula II. Typically this is accomplished using p-carboxybenzenesulfonylazide in the presence of an acid acceptor. Preferred temperatures range from about −5° to about 5° C. Preferred solvents are halogenated hydrocarbons such as methylene chloride and chloroform.

The following preparations and examples describe in detail the compounds of the present invention and processes for their preparation. It will be apparent to those skilled in the art that many modifications, both of materials and methods, may be practiced without departing from the spirit and scope of the invention. Throughout these preparations and examples, "NMR" denotes nuclear magnetic resonance spectra; "MS" denotes mass spectra; "UV" denotes ultraviolet spectra; and "IR"

denotes infrared spectra. Chromatography is performed on silica gel unless otherwise denoted.

PREPARATION A

A. 1-(t-butyldimethyl)silyl-4-allylazetidin-2-one:

t-Butyldimethylsilylchloride (7.25 g) is added to a solution of 4-allylazetidin-2-one (5 g) in methylene chloride (50 ml) and triethylamine (5 ml) at 0° C. The mixture is stirred for 2 hours, washed successively with water and brine, dried and evaporated to afford the title product as a colorless oil having IR: 5.70; NMR: (CDCl$_3$) 0.2(3H), 1.0(6H).

B. 1-(t-butyldimethyl)silyl-3(S)-[1'R)-hydroxyethyl]-4(R)-allylazetidin-2-one:

A solution of 1-(t-butyldimethyl)silyl-4-allylazetidin-2-one 22.4 g) in tetrahydrofuran (200 ml) at −76° C. is added during 10 minutes to a cold solution (−76° C.) of lithium diisopropylamide prepared from 2.5 M butyllithium (44 ml) and diisopropylamine (15.4 ml) in dry tetrahydrofuran (380 ml). After stirring for 10 minutes, freshly distilled acetaldehyde (12 ml) is added to the reaction mixture. The reaction is quenched after 60 seconds by adding saturated solution of ammonium chloride (150 mg), allowed to warm to 0° C. and then extracted three times with 250 ml portions of ethyl acetate. The extracts are combined, washed with brine, dried and the solvents removed. The resulting oil is separated by preparative HPLC on 2 Prep. 500 silica gel columns using 30:60 ethyl acetate-hexane as solvent to afford the desired compound as an oil, having IR: 5.70; NMR: (CDCl$_3$) 0.2(3H), 1.0(6H), 1.28(d,3H,J=6 cps), 2.85 (dd,1H,J=6;3 cps); MS: 270 (M+ +1). The 1'(S) isomer (3.5 g) and the 4(S) isomer (3.8 g) which are formed in the reaction, are separable from the desired compound.

C. 1-(t-Butyldimethyl)silyl-3(S)-[(1'R)-2,2,2-trichloroethoxycarbonyloxyethyl]-4(R)-allylazetidin-2-one:

A solution of 1-(t-butyldimethyl)silyl-3(S)-[(1'R)-hydroxyethyl]-allylazetidin-2-one (8 g) in methylene chloride (80 ml) is cooled to 0° C. and treated with pyridine (3.4 ml), followed by dropwise addition of trichloroethoxychloroformate (6.5 ml). The mixture is stirred for 1 hour, washed three times with 20 ml portions of water and then brine, dried and evaporated to afford the title compound as an oil having IR: 5.75; NMR: (CDCl$_3$) 4.72(s, 2H), 3.0 (dd, 1H, J=7; 3 cps); MS: 386, 388 (M+ −57).

D. 1-(t-butyldimethyl)silyl-3(S)-[(1'R)-2,2,2-trichloroethoxycarbonyloxyethyl]-4(R)-(2''-ethanal)azetidin-2-one:

Ozonized oxygen is bubbled thru a solution of 1-(t-butyldimethyl)silyl-3(S)-[(1'R)-2,2,2-trichloroethoxycarbonyloxyethyl]-4(R)-allylazetidin-2-one (14 g) in methylene chloride (80 ml) at −76° C. until layer chromatography (silica gel plates, 40:60 ethyl acetate:hexane) indicates disappearance of starting material. Excess ozone is swept off the solution with a stream of nitrogen followed by addition of dimethylsulfide (8 ml). The solution is allowed to stand at room temperature overnight and then is evaporated to afford the title compound as an oil having NMR: (CDCl$_3$) 3.06(dd, 1H, J=7.3 cps); 7.20 (S, 1H); MS: 388, 390 (M+ −57).

E. 1-(t-butyldimethyl)silyl-3(S)-[(1'R)-2,2,2-trichloroethoxycarbonyloxyethyl]-4(R)-(allyl-3''-hydroxy-4''-butyrate)azetidin-2-one:

Allyl acetate (1 ml) is added to a solution of lithium diisopropylamide (prepared by added 2.8 ml of a 2.5 M solution n-butyllithium to 1 ml diisopropylamide in 20 ml tetrahydrofuran) at −70° C. followed after 10 minutes by a solution of 1-(t-butyldimethyl)silyl-3(S)-[(1'R)-2,2,2-trichloroethoxycarbonyloxyethyl]-4(R)-(2''-ethanal)azetidin-2-one (2.0 g) in tetrahydrofuran (40 ml). The reaction is allowed to proceed for 15 minutes at −78° C. and is then worked up by adding acetic acid (2 ml), saturated sodium chloride solution (60 ml) and extracting three times with 50 ml portions of ether. The ether extract is washed with brine, dried and evaporated. The residual oil is chromatographed on 70 g silica gel. Elution with 30:70 ethyl acetate-hexane affords the title compound as a colorless oil having IR: 5.75; NMR: (CDCl$_3$) 5.94(dd, 1H, J=8; 3 cps) 4.6(d,2H, J=6 cps), 5.3 (m,2H), 5.9 (m,1H); MS: 488, 490 (M+ −57).

F. 1-(t-Butyldimethyl)silyl-3(S)-[(1'R)-2,2,2-trichloroethoxycarbonyloxyethyl]-4(R)-(allyl-3''-Keto-4''-butyrate)azetidin-2-one:

Chromium trioxide (12 g) is added in small portions to a solution of pyridine (19 g) in methylene chloride (300 ml). The resulting dark red solution is stirred vigorously for 15 minutes and is added to a solution of 1-(t-butyldimethyl)silyl-3(S)-[(1'R)-2,2,2-trichloroethoxycarbonyloxyethyl]-4(R)-(allyl-3''-hydroxy-4''-butyrate)azetidin-2-one (5.0 g) in methylene chloride (20 ml). The mixture is stirred until thin layer chromatography (silica-gel, 50:50 ether:hexane) indicates disappearance of starting material. The solution is filtered thru 60 g silica gel and the eluate is washed with diluted hydrochloric acid, brine, dried and evaporated to afford the title compound as a colorless oil having NMR: (CDCl$_3$) 3.4(s, 2H). MS: 486, 488 (M+ −57)

G. 3-(S)-[(1'R)-Hydroxyethyl]-4(R)-(allyl-3''-keto-4''-butyrate)azetidin-2-one:

A solution of 1-(t-butyldimethyl)silyl-3(S)-[(1'R)-2,2,2-trichloroethoxycarbonyloxyethyl]-4(R)-(allyl-3''-keto-4''-butyrate)azetidin-2-one (2.7 g) in a mixture of tetrahydrofuran (27 ml), glacial acetic acid (16 ml) and water (6.0 ml) is cooled to −20° C. (dry ice/carbon tetrachloride) and stirred wth zinc dust (3.0 g) added in portions over 1 hour. The suspension is stirred for 3 hours, diluted with ethylacetate (50 ml) and filtered. The filtrate is washed with cold 10% aqueous sodium bicarbonate, brine, dried and evaporated. The resultant oil is dissolved in tetrafuran (40 ml) and stirred with 20 ml 401-S Fluoride resin (obtained by Neutralizing Rohm & Haas' AMBERLITE 401-S resin with hydrofluoric acid and washing the resulting fluoride resin with water until washings are neutral) for 3 hours. The resin is then removed by filtration and the filtrate on evaporation to afford the title compound having IR: 5.65, 5.78; NMR: (CDCl$_3$) 3.5(s, 2H).

H. 3(S)-[(1'R)-Hydroxyethyl]-4(S)-(allyl-2''-diaza-3''-ketobutyrate)azetidin-2-one:

A solution of 3(S)-[(1'R)-hydroxyethyl]-4(R)-(allyl-3''-keto-4''-butyrate)azetidin-2-one (0.68 g) and p-carboxybenzenesulfonylazide (0.6 g) in methylene chloride (10 ml) is cooled to 0° C. and treated dropwise with triethylamine (0.9 ml). The mixture is then stirred at room temperature until thin layer chromatography (silica gel plate, 25% acetone/chloroform) indicated disappearance of starting material. The reaction mixture is then diluted with ether, washed with 10% aqueous sodium bicarbonate, brine, dried and evaporated to afford the title product as an oil having IR: 5.62, 5.75, 5.80.

PREPARATION I

By substantial repetition of the process described in Preparations A-H, utilizing the appropriate starting materials, the following compounds of the formula are prepared:

[Structure: R$_4$-C(=O)-NH-CH(H)(R$_4'$...)-N$_2$-C(=O)-COOR$_8$, with two H's on the central carbon]

| R$_4$ | R$_8$ |
|---|---|
| TCEO-CH(-)-C$_6$H$_5$ | -CH$_2$-CH=CH$_2$ |
| TCEO-CH(-)-(pyridyl) | -CH$_2$-CH=CH$_2$ |
| N-C$_6$H$_4$-CH$_2$-CH(TCEO)- | -CH$_2$-C$_6$H$_4$-NO$_2$ |
| CH$_3$-CH$_2$- | -CH$_2$-CH=CH$_2$ |
| CH$_3$O- | -CH$_2$-CH=CH$_2$ |
| TCEO-CH(CH$_3$)- | -CH$_2$-CH=CH$_2$ |
| H- | -CH$_2$-CH=CH$_2$ |

TCE = trichloroethoxycarbonyl

PREPARATION J

Bis(N-allyloxy carbonyl)-L-cystine bis-allyl ester

A solution of L-cystine (12 g) in a 4 N sodium hydroxide (25 ml) at ice bath temperature is stirred while allyl chloroformate (10.6 ml) and 4 N sodium hydroxide (25 ml) are added dropwise. The mixture is stirred for 30 mins. after the final addition and is then washed with 50 ml of ether. The aqueous phase is then acidified to pH 2 with 1 N hydrochloric acid and extracted with 3×50 ml ether. The ether extracts are dried with sodium sulfate and evaporated. The residual colorless oil is dissolved in acetone (75 ml) containing triethylamine (9.6 ml) and stirred while allyl bromide (6.0 ml) is added dropwise. The mixture is stirred overnight, diluted with ethylacetate (75 ml) and brine (75 ml). The aqueous phase is extracted three times with ethyl acetate. The organic extracts are washed with 1 N sodium hydroxide, 1 N hydrochloric acid, water, dried with sodium sulfate and evaporated. The title product is crystallized from ether-hexane as colorless needles, with a m.p. of 47°-48° C. and an $[\alpha]_D$ of +55° (chloroform).

PREPARATION K

N-allyloxycarbonyl-L-cysteine allyl ester

A suspension of zinc dust (8 g) in a solution of bis(N-allyloxylcarbonyl)-L-cystine bis allyl ester (7.56 g) in methanol (50 ml) at 0° C. is stirred vigorously while adding concentrated hydrochloric acid (5 ml) in one portion. After 2 minutes the mixture is diluted with ice water and extracted with 3×50 ml of chloroform. The extracts are dried over sodium sulfate and evaporated under reduced pressure to afford the title products.

PREPARATION L

Bis(N-allyloxycarbonyl)-D-cystine bis allyl ester

Following the procedure described in Preparation A utilizing D-cystine as starting material there is obtained the title products, having a melting point of 48°-49° C. and an $[\alpha]_D$=55° (chloroform).

PREPARATION M

N-allyloxycarbonyl-D-cysteine allyl ester

A suspension of zinc dust (5.18 g) in a solution of bis(N-allyloxycarbonyl-D-cystine bis-allyl ester (5.18 g) in methanol (50 ml) at 0° C. is stirred vigorously while adding concentrated hydrochloric acid (3.5 ml) in one portion. After two minutes, the mixture is worked up as in the above Preparation B to afford the title product.

PREPARATION N

N-allyloxycarbonylsulfanyl-D-cysteine allyl ester

A solution of D-cystine (12 g) in 4 N sodium hydroxide (25 ml) is stirred at 0° while N-allyloxycarbonylsulfanilyl chloride (30 g) and 4 N sodium hydroxide (25 ml) is added dropwise. The mixture is stirred for 30 minutes, acidified with 1 N hydrochloric acid, extracted with ether and the extract evaporated. The residual oil is dissolved in acetone (75 ml) containing triethylamine (9.6 ml) and stirred while allyl bromide (6.0 ml) is added dropwise. This mixture is stirred overnight, diluted with ethyl acetate and the organic layer is washed with 1 N sodium hydroxide, 1 N hydrochloric acid, brine, dried over sodium sulfate and evaporated to afford bis N-allyloxycarbonylsulfanyl-D-cystine bis allyl ester. Treatment of this bis compound with zinc dust according to the procedure of Preparation I affords the title compound.

PREPARATION O (N-methyl-N-allyoxycarbonyl)-D-cysteine allyl ester

A solution of bis(N-allyloxycarbonyl)-D-cystine bis allyl ester (4.8 g) in dimethyl sulfoxide (40 ml) is added to a solution of sodium hydride (0.5 g) in dimethylsulfoxide (40 ml). The reaction is stirred under nitrogen while adding methyliodide (50 ml). After 15 minutes the mixture is diluted with ice/water, extracted with ethylacetate and extracts are washed with brine, dried over sodium sulfate and evaporated to afford bis(N-methyl-N-allyloxycarbonyl)-D-cystine bis allyl ester. Treatment of this bis compound according to the procedure of Preparation I affords the title compound.

PREPARATION P

N-acetyl-D-cysteine allyl ester

A solution of bis-N-acetyl D-cystine (3.2 g) in acetone (30 ml) containing triethylamine (4.0 g) is stirred with allyl bromide (4 ml) for 24 hours. The mixture is diluted with water, washed with 1 N sodium hydroxide, 1 N hydrochloric acid, brine, dried over sulfate and evaporated to afford bis N-acetyl-D-cystine bis allyl ester. Treatment of this bis compound accoding to the procedure of Preparation I affords the title compound.

EXAMPLE 1

(5R,6S,8R,2′S)-2-[2′-amino-2′-carboxyethyl]thio-6-(1-hydroxyethyl)-1-carbapen-2-em-3-carboxylic acid, sodium salt A. A solution of 3(S)-[(1′R)-hydroxyethyl]-4(S)-(allyl-2″-diaza-3″-ketobutyrate)azetidin-2-one (0.5 g) in benzene (100 ml) containing rhodium acetate (0.004 g) is stirred at 80° for 10 minutes until thin layer chromatography indicates complete reaction (silica-gel plates, 10:90 acetone/chloroform). The solution is cooled to room temperature, washed with water, brine, dried and evaporated to afford allyl 6(S)-[(8R)-hydroxyethyl]-1-carba-2-oxopenam-3-carboxylate (0.4 g) which is immediately dissolved in dichloromethane (5 ml) and cooled to 0° C. Then, to this is added dropwise, with stirring, diisopropylethylamine (0.2 g), followed by diphenylchlorophosphate (0.42 g). The mixture is stirred at 0° C. until thin layer chromatography indicates completion of reaction to form allyl 6(S)-[(8R)-hydroxyethyl]-1-carba-2-diphenylphosphatoxypen-2-em-3-carboxylate. The mixture is then treated with N-allyloxycarbonyl-D-cystein allyl ester (0.4 g) and diisopropylethylamine (0.2 g). Stirring is continued until thin layer chromatography (silica gel, 5:95 acetone: chloroform) shows that reaction is complete. The mixture is then washed with brine, concentrated to 5 ml and immediately used in the next step.

B. The solution from the above step is diluted with a 1 M solution of pyridinium formate in methylene chloride (7.5 ml) and stirred with tetrakis(triphenylphosphine) palladium (0.2 g) and triphenylphosphine (0.2 g) for 20 minutes. The resulting precipitate is then collected and washed with 6 times with methylene chloride by centrifugation and suspended in a 0.5 M solution of sodium 2-ethylhexanoate in ethyl acetate (2 ml) for 1 hour. The precipitate is then collected after washing by centrifugation, three times with ethyl acetate and then with ether and dried in vacuo to afford the title product having IR: 5.68, 6.1.

EXAMPLE 2

Repetition of the procedure detailed in Example 1 using the appropriate starting materials afford the following compounds of the formula:

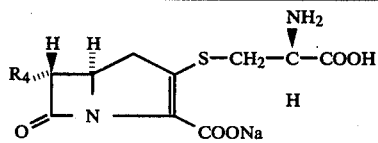

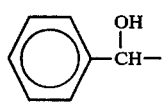

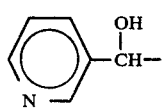

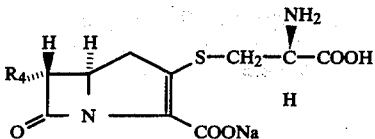

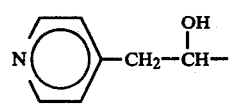

CH₃CH₂—
CH₃O—

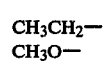

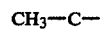

H—

EXAMPLE 3

(5R,6S,8R,2′R)-2-[(2′-acetimidoyl-2′-carboxyethyl)thio]-6-(1-hydroxyethyl)-1-carbapen-2-em-3-carboxylate, disodium salt A solution of (5R,6S,8R,2′R)-2[(2′-amino-2′carboxyethyl)thio]6-(1-hydroxyethyl)1-carbapen-2-em-3-carboxylate, sodium salt (75 mg) in water (2 ml) is treated with ethylacetimidate (100 mg) at 20° C. The solution is chromatographed on Dowex 50×4 (Na+ form), eluted with water, and fractions containing title compound are lyophilized to give the title compound.

EXAMPLE 4

(5R,6S,8R,2′R)-2-[(2′-guanidoyl-2′-carboxyethyl)thio]-6-(1-hydroxyethyl)-1-carbapen-2-em-3-carboxylate, disodium salt A solution of (5R,6S,8R,2′R)-2-[(2′-amino-2′carboxyethyl)thio]-6-1(1-hydroxyethyl-1-carbapen-2-em-3-carboxylate, sodium salt (75 mg) in water (2 ml) and S-benzylisothiourea hydrochloride (50 mg) is stirred at room temperature. The solution was chromatographed on Amberlite 401-S (sodium form), eluted with water and fractions containing title compound are lyophilized to give the title compound.

EXAMPLE 5

(5R,6S,8R,2′R)-2-[(2′-(ethyl-3″-aminoyl-but-2″-enoate)2′carboxyethyl thio]-6-(1-hydroxyethyl)-1-carbapen-2-em-3-carboxylate, disodium salt A solution of (5R,6S,8R,2′R)-2-[2′-amino-2′-carboxyethyl)thio]-6-(1-hydroxyethyl)1-carbapen-2-em-3-carboxylate, sodium salt (100 mg) in water (0,5 ml) and ethyl acetoacetate (130 mg) is stirred at room temperature for several hours and then washed with ethyl acetate. The aqueous layer, upon lyophilization, affords the title compound.

EXAMPLE 6

(5R,6S,8R,2'S)-2-[(2'-sulfanilamidoyl-2'-carboxyethyl)-thio]-2-(1hydroxyethyl-1-carbapen-2-em-3-carboxylate, sodium salt Using N-allyloxycarbonylsulfanyl-D-cysteine allyl ester, the procedure of paragraphs A-B of Example 1 are repeated to afford the title compound.

EXAMPLE 7

(5R,6S,8R,2'R)-2-[(2'-benzazabethinyl-2'-carboxyethyl)thio]-6-(1-hydroxyethyl)-1-carbapen-2-em-3-carboxylate, diosodium salt A solution of (5R,6S,8R,2'R)-2-[(2'-amino-2'-carboxyethyl)thio]-6-(1-hydroxyethyl)-1-carbapen-2-em-3-carboxylate, sodium salt (100 mg) in methanol (0.5 ml) and benzaldehyde (200 mg) is stirred at room temperature for several hours, diluted with water, washed with ethyl acetate and the aqueous layer is lyophilized to afford the title compound.

EXAMPLE 8

(5R,6S,8R,2'S)-2-[(2'-methylamino-2'-carboxyethyl)thio]-6-(1-hydroxyethyl)-1carbapen-2-em-3-carboxylate, sodium salt Repetition of the procedure detailed in paragraphs A-B of Example 1 utilizing (N-methyl-N-allyloxycarbonyl)-D-cysteine allyl ester affords the title compound.

EXAMPLE 9

(5R,6S,8R,2'R)-2-[(N-carbobenzyloxy-2'-amino-2'-carboxyethyl thio]-6-(1-hydroxethyl)-1-carbapen-2-em-3-carboxylate, disodium salt A solution of (5R,6S,8R,2'R)-2-[(2'-amino-2'-carboxyethyl)thio]-6-(1-hydroxyethyl)-1-carbapen-2-em-3-carboxylate, sodium salt (100 mg) in water (2 ml) is stirred at 0° C. with benzylchloroformate (0.2 ml). The reaction is washed with ethyl acetate and aqueous solution is chromatographed on Amberlite 401-S (sodium form). Fractions containing the title compound are lyophilized to give the pure title compound.

EXAMPLE 10

(5R,6S,8R,2'S)-2-[(2'-acetylamino-2'-carboxyethylthio]-6-(1-hydroxyethyl)-1-carbapen-2-em-3-carboxylate, disodium salt Substantial repetition of the procedure of paragraphs A-B of Example 1 utilizing N-acetyl-D-cystine allyl ester affords the title compound.

The following formulations are to exemplify some of the dosage forms in which the antibacterial agents of this invention may be employed. In each, the active ingredient is designated by the term "Drug" which is meant to indicate (5R,6S,8R)2'S-2-[2'-amino-2'-carboxyethyl)thio]-6-(1-hydroxyethyl)-1-carbapen-2-em-3-carboxylic acid, sodium salt or an equally effective quantity of any other compounds defined by formula I.

EXAMPLE 11

Injection Formulation
Per vial: Drug (Sterile powder)
   Add sterile water for injection U.S.P. or bacteriostatic water for injection U.S.P., for reconstitution.

EXAMPLE 12

| Injectable Suspension Formulation | mg/mg |
|---|---|
| Sterile drug | 250.0 |
| Benzyl Alcohol | 9.0 |
| Methylparaben | 1.8 |
| Propylparaben | 0.2 |
| Sodium Carboxymethylcellulose | 5.0 |
| Polyethylene Glycol 4000 | 10.0 |
| Povidone | 5.0 |
| Sodium Citrate | 15.0 |
| Disodium Edetate | 0.1 |
| Water for Injection | q.s. |
| To make | 1.0 ml |

Dissolve parabens in a portion of the water for injection by heating it to 65°-70° C. Cool to 25°-35° C. Charge and dissolve benzyl alcohol, sodium citrate, disodium edetate, PEG 4000, povidone and sodium carboxymethylcellulose. Filter the solution and sterilize by autoclaving. Make a slurry of the sterile active and passit through the mill. Bring the suspension to the final volume/weight and fill into sterile containers.

EXAMPLE 13

| | Capsule Formulation | | |
|---|---|---|---|
| Item No. | Ingredient | mg/capsule | mg/capsule |
| 1 | Drug | 250 | 500 |
| 2 | Lactose, USP | 106 | 123 |
| 3 | Corn Starch, Food Grade | 40 | 70 |
| 4 | Magnesium Stearate, USP | 4 | 7 |
| | | 400 mg | 700 mg |

Mix Item Nos.s. 1, 2 and 3 in a suitable mixer for 10-15 minutes. Add Item No. 4 and mix for 1-3 minutes. Fill the above mixture into suitable 2-piece hard gelatin capsules.

EXAMPLE 14

| | Tablet Formulation | | |
|---|---|---|---|
| Item No. | Ingredient | mg/tablet | mg/tablet |
| 1 | Drug | 250 | 500 |
| 2 | Lactose, USP | 106 | 112 |
| 3 | Corn starch, Food Guide as 10% paste in water | 20 | 40 |
| 4 | Corn starch, Food Guide | 20 | 40 |
| 5 | Magnesium Stearate | 4 | 8 |
| | | 400.0 mg | 800.0 mg |

Mix Item Nos. 1 and 2 in a suitable mixer for 10-15 minutes. Granulate the mixture with Item No. 3. Pass the wet granulation through a coarse screen (¼"). Dry the wet granules for 8-12 hours at 40°-50° C. Using a suitable mill, pass the dried granules through a medium screen (No. 12 to No. 16). Add Item No. 4 and mix for 10-15 minutes. Add Item No. 5 and mix further for 1-3 minutes. Compress the mixture to appropriate size and weight on a suitable tablet machine.

What is claimed is:

1. (5R,6S,8R,2'S)-2-[(2'-amino-2'-carboxyethyl)thio]-6-(1-hydroxyethyl)-1-carbapen-2-em-3-carboxylic acid, sodium salt.

2. A pharmaceutical composition comprising an antibacterially effective amount of (5R,6S,8R,2'S)-2-[2'- amino-2'-carboxyethyl)thio]-6-(1-hydroxyethyl)-1-carbapen-2-em-3-carboxylic acid, sodium salt together with a non-toxic pharmaceutically acceptable carrier.

3. A method of eliciting an antibacterial response in a warm-blooded animal to a susceptible bacterial infection which comprises administering to said animal a non-toxic antibacterially effective amount of (5R,6S,8R,2'S)-2-[2'-amino-2'-carboxyethyl)thio]-6-(1-hydroxyethyl)-1-carbapen-2-em-3-carboxylic acid, sodium salt, together with a non-toxic pharmaceutically acceptable carrier.

* * * * *